United States Patent [19]

DeHaven-Hudkins et al.

[11] Patent Number: 5,290,789
[45] Date of Patent: Mar. 1, 1994

[54] PENTA AND TETRASUBSTITUTED PIPERIDINES AND COMPOSITIONS AND METHOD OF TREATING PSYCHOSIS

[75] Inventors: Diane L. DeHaven-Hudkins, Chester Springs, Pa.; John P. Mallamo, Kinderhook; William F. Michne, Poestenkill, both of N.Y.; Martha R. Heimann, Durham, N.C.

[73] Assignee: Sterling Wintrop Inc., New York, N.Y.

[21] Appl. No.: 979,027

[22] Filed: Nov. 20, 1992

[51] Int. Cl.$^5$ .................. A61K 31/445; C07D 211/22
[52] U.S. Cl. ..................................... 514/317; 514/315; 546/236; 546/248
[58] Field of Search ............... 546/236, 248; 514/315, 514/317

[56] References Cited

U.S. PATENT DOCUMENTS

| | | | |
|---|---|---|---|
| 3,097,212 | 7/1963 | Jucker | 546/236 |
| 3,422,451 | 1/1969 | Cope | 546/248 |
| 3,431,267 | 3/1969 | Welcher | 546/246 |
| 5,023,266 | 6/1991 | Langer et al. | 514/317 |

FOREIGN PATENT DOCUMENTS

| | | |
|---|---|---|
| 449187 | 10/1991 | European Pat. Off. . |
| 445195 | 11/1991 | European Pat. Off. . |
| 9202501 | 2/1992 | World Int. Prop. O. . |

OTHER PUBLICATIONS

Schneider et al "Preparation of 3(4-Hydroxyl Alkyl) Substituted N-piperidines", CA 68: 21794f (1968).

Yanina et al "Hofmann Degradation of 1-Azabycyclo[3,2,1] Octane" CA 58: 13909g (1963).
Cervinka "Enamines. V." CA 55: 4507c (1961).
Loew, et al., Endog. Exog. Opiate Agonists and Antagonists, E. L. Way, editor, Pergamon: Elmsford, New York 1980, pp. 39–42.
Glennon, et al., J. Med. Chem. 1991, 34, 3360–3365.

*Primary Examiner*—C. Warren Ivy
*Assistant Examiner*—Celia Chang
*Attorney, Agent, or Firm*—Michael D. Alexander; Paul E. Dupont

[57] ABSTRACT

The invention is related to compounds, being useful in treating psychosis, of the formula:

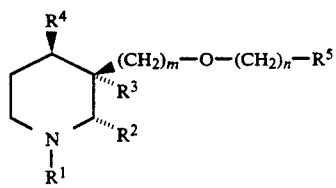

wherein:
$R^1$ is hydrogen, lower-alkyl or phenyl-lower-alkyl;
$R^2$ and $R^4$ are the same or different lower-alkyl;
$R^3$ is hydrogen or lower-alkyl;
m is two or three;
n is an integer from zero to three; and
$R^5$ is hydrogen, lower-alkyl, $C_3$–$C_7$-monocyclic cycloalkyl, allyl, or propargyl;
or a pharmaceutically acceptable acid-addition salt thereof.

15 Claims, No Drawings

PENTA AND TETRASUBSTITUTED PIPERIDINES AND COMPOSITIONS AND METHOD OF TREATING PSYCHOSIS

BACKGROUND OF THE INVENTION

1. Field of the Invention

The invention relates to novel penta and tetrasubstituted piperidines, to compositions containing the same, to the method of use thereof in the treatment of central nervous system disorders, and to processes for their preparation.

A number of know antipsychotic drugs are disclosed in the art which have been shown to share a selective, high affinity for sigma receptors, which are sites where psychotomimetic opiates, such as (+)-pentazocine and N-allylnormetazocine, act. It has been suggested that the antipsychotic behavioral profile of these antipsychotic drugs can be attributed to their role as competitive antagonists of sigma receptor binding and that a systematic screen for drugs that block sigma receptors may provide a valuable strategy for identifying novel antipsychotic agents. Additionally, it has been shown that the relative potencies of these agents studied in vivo correspond well with their relative binding affinities obtained in vitro. See, for example, Synder and Largent, J. Neuropsychiatry 1989, 1(1), 7-15; Largent, et al., Eur. J. Pharmacol. 1988, 155, 345-347; Deutsch, et al., Clinical Neuropharmacology 1988, 11(2), 105-119; Tayler, et al., Drug Development Research 1987, 11, 65-70; Ferris, et al., Life Sciences 1986, 38(25), 2329-2337; and Su, et al., Neuroscience Letters 1986, 71, 224-228.

2. Information Disclosure Statement

Welcher, U.S. Pat. No. 3,431,267, issued Mar. 4, 1969, discloses 2,3-dimethyl-3-piperidinepropanamine

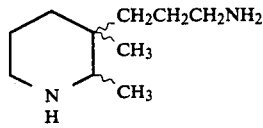

as a fungicide and pesticide.

Loew, et al., Endog. Exog. Opiate Agonists and Antagonists, E. L. Way, editor, Pergamon:Elmsford, New York 1980, pp 39–42, disclose 1-$R_1$-2,3,4,4-tetramethylpiperidines of general formula

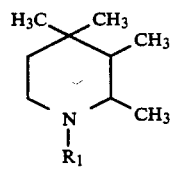

wherein $R_1$ is 3-furanylmethyl, 2-furanylmethyl, 2-propenyl, cyclopropylmethyl, phenylethyl, methyl and hydrogen without an indication of utility.

Langer, et al., U.S. Pat. No. 5,023,266, issued Jun. 11, 1991, disclose compounds of the formula:

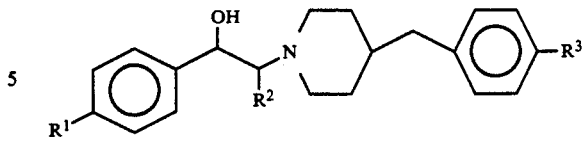

wherein:
- $R^1$ denotes a halogen atom or a hydroxy group;
- $R^2$ denotes a hydrogen atom or a methyl group; and
- $R^3$ denotes a hydrogen or halogen atom.

The compounds are said to be useful in the treatment of psychotic disorders.

Gray and Cheng, European Patent Application 455195, published Nov. 6, 1991, disclose a series of ethanobicyclic amine derivatives which are said to be useful in the treatment of CNS disorders such as psychotic disorders, convulsions, dystonia and cerebral ischemia.

Cain, et al., European Patent Application 449187, published Oct. 2, 1991, disclose a series of disubstituted piperidine ether derivatives which are said to be useful in treating physiological or drug induced psychosis or dyskinesia in mammals or fungal disease in plants. Glennon, et al., J. Med. Chem. 1991, 34, 3360–3365, disclose a series of novel 4-phenylpiperidine derivatives which are stated to bind with high affinity to sigma receptors.

SUMMARY OF THE INVENTION

The invention relates to compounds of Formula I:

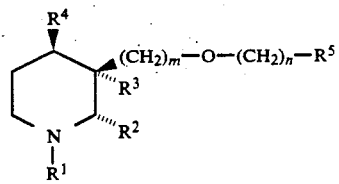

wherein
- $R^1$ is hydrogen, lower-alkyl or phenyl-lower-alkyl;
- $R^2$ and $R^4$ are the same or different lower-alkyl;
- $R^3$ is hydrogen or lower-alkyl;
- m is two or three;
- n is an integer from zero to three; and
- $R^5$ is hydrogen, lower-alkyl, cycloalkyl, allyl, or propargyl;

or a pharmaceutically acceptable acid-addition salt thereof.

The compounds of the present invention bind with high affinity to sigma receptors and are thus useful in the treatment of central nervous system disorders.

Preferred compounds of Formula I above are those wherein:
- $R^1$, m, n, and $R^5$ are as defined above; $R^2$ and $R^4$ are methyl; $R^3$ is hydrogen or methyl; and $R^5$ is hydrogen, cycloalkyl, allyl, or propargyl.

Particularly preferred compounds of Formula I above are those wherein:
- $R^1$ is hydrogen, methyl, propyl, isopropyl or benzyl;
- $R^2$ and $R^4$ are methyl;
- $R^3$ is hydrogen or methyl;
- m is two or three;
- n is zero or one; and
- $R^5$ is hydrogen, methyl, cyclopropyl, allyl or propargyl.

The invention further relates to pharmaceutical compositions which comprise a compound of Formula I together with a pharmaceutically acceptable carrier, adjuvant, diluent or vehicle.

The invention further relates to a method for the treatment of central nervous system disorders, especially psychoses, which comprises administering to a patient in need of such treatment an effective amount of a compound of Formula I.

The invention further relates to a process for preparing a compound of Formula I which comprises the steps of:

(a) reacting a compound of Formula VII:

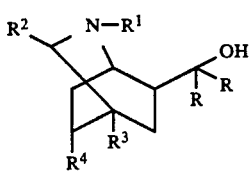

VII wherein R is lower-alkyl, with formic acid in the presence of a base to produce a compound of Formula VI;

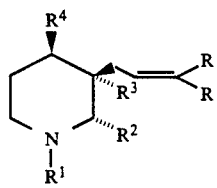

VI (b) thereafter reacting said compound of Formula VI with ozone, followed by a reducing agent to produce a compound of Formula V;

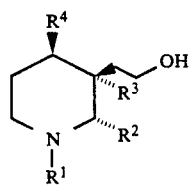

V and (c) treating said compound of Formula V with an alkylating agent, $R^5(CH_2)_nX$ wherein X is Cl, Br or I, in the presence of a base and a phase transfer catalyst to produce a compound of Formula I wherein m is 2.

The invention further relates to a process for preparing a compound of Formula I, which comprises the steps of:

(a) reacting a compound of Formula IV:

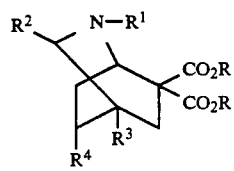

IV wherein R is lower-alkyl, with formic acid in the presence of a base to produce a compound of Formula III;

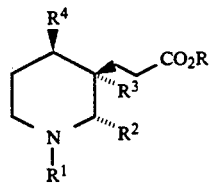

III (b) thereafter reacting said compound of Formula III with a reducing agent to produce a compound of Formula II;

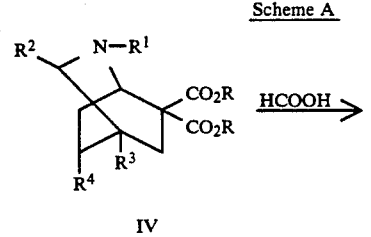

II and (c) thereafter reacting said compound of Formula II with an alkylating agent, $R^5(CH_2)_nX$ wherein X is Cl, Br, or I, in the presence of a base and optionally in the presence of a tetraalkylammonium halide to produce a compound of Formula I wherein m is 3.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec butyl and the like.

The term cycloalkyl as used herein means monocyclic hydrocarbon ring systems having three to about seven carbon atoms and thus includes cyclopropyl, cyclobutyl, cyclopentyl, cyclohexyl and cycloheptyl.

The term halogen, halide or halo as used herein means fluorine, chlorine, bromine and iodine.

The compounds of the invention wherein m is three are prepared as shown in Scheme A:

Scheme A

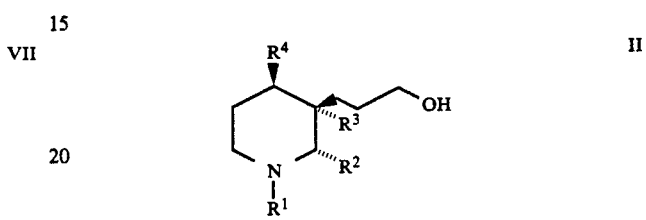

IV

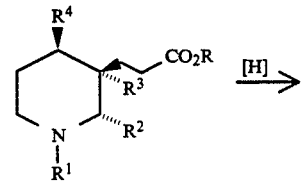

III

-continued
Scheme A

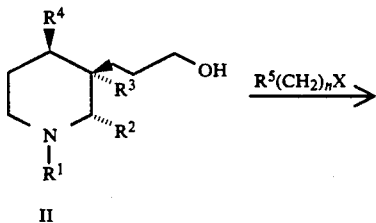

II

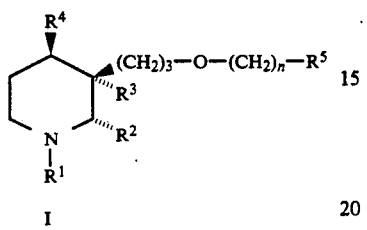

I

A suitably substituted dilower-alkyl 2-azabicyclo[2.2.-2]octane-6,6-dicarboxylate (IV, R=lower-alkyl, preferably ethyl), is treated with an excess of formic acid, and an excess of a base preferably triethylamine, in the absence of a solvent, at a temperature in the range of from about 110° C. up to about 160° C. to produce a lower-alkyl 3-(3-piperidine)propanoate of the Formula III. The propanoate of Formula III is treated with an excess of a reducing agent, e.g. lithium aluminum hydride, in a solvent, e.g. tetrahydrofuran, at a temperature in the range of about 0° C. up to about 25° C. to produce the corresponding substituted 3-(3-piperidine)propanol of Formula II. The compound of Formula II is then treated with an excess of an appropriate alkylating agent, $R_5(CH_2)_nX$ wherein X is Cl, Br, or I, in the presence of an excess of a base, preferably potassium hydride, optionally in the presence of about 1–5 mole percent of a tetraalkylammonium halide, preferably tetrabutylammonium iodide, in a solvent such as tetrahydrofuran, at a temperature in the range of about −25° C. up to about 25° C. to produce a compound of Formula I wherein m is three. Alternatively and preferably, the compounds of Formula I wherein m is 3, n is zero and $R^5$ is methyl are obtained by reacting a compound of the Formula II with an excess of dimethyl sulfate, in the presence of an excess of a base, preferably potassium hydride, in a solvent, such as tetrahydrofuran, at a temperature in the range of about 0° C. up to the boiling point of the solvent used. It will of course be appreciated that when compounds of the Formula I wherein $R^1$ is hydrogen are desired, it is preferred to prepare a compound of the Formula I wherein $R^1$ is benzyl as described hereinabove and then to remove the benzyl group by catalytic hydrogenation.

The compounds of the invention wherein m is two are prepared as shown in Scheme B:

Scheme B

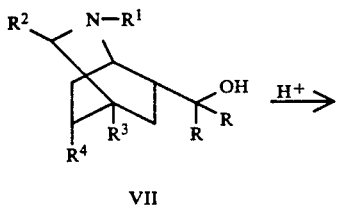

VII

-continued
Scheme B

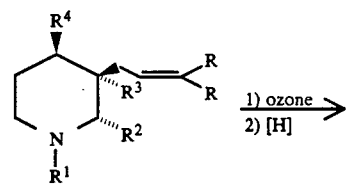

VI

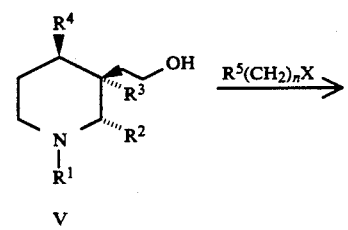

V

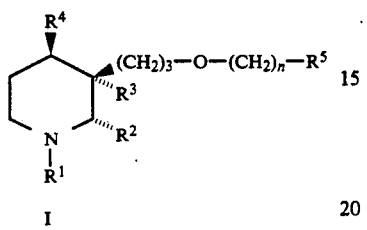

I

A suitably substituted 2-azabicyclo[2.2.2]octane-6-lower-alkanol (VII, R is lower-alkyl, preferably methyl) is treated with an excess of formic acid, in the presence of an excess of a base, preferably triethylamine, in the absence of a solvent, at a temperature in the range of about 120° C. up to the boiling point of the formic acid/triethylamine mixture to produce the substituted 3-allylpiperidine of Formula VI. Treatment of the compound of Formula VI with ozone, in an alcoholic solvent, e.g. ethanol, followed by treatment with an excess of a reducing agent, e.g. sodium borohydride, at a temperature in the range of about −78° C. to about 25° C. produces the 3-piperidineethanol of Formula V. Treatment of the compound of Formula V with an excess of an alkylating agent, $R^5(CH_2)_nX$, in the presence of an excess of a base, preferably sodium hydride, additionally in the presence of about 5 mole percent of a phase transfer catalyst, preferably tris[2-(2-methoxy)-ethoxyethyl]amine, in a solvent such as tetrahydrofuran at a temperature in the range of about 25° C. up to the boiling point of the solvent used, produces the compounds of Formula I wherein m is two. As before, it will be appreciated that when compounds of the Formula I wherein $R^1$ is hydrogen are desired, it is preferred to prepare a compound of the Formula I wherein $R^1$ is benzyl as described hereinabove and then to remove the benzyl group by catalytic hydrogenation.

In those instances wherein it is desirable to prepare a compound of the Formula I wherein $R^1$ is lower-alkyl it is convenient to proceed as shown in Scheme C:

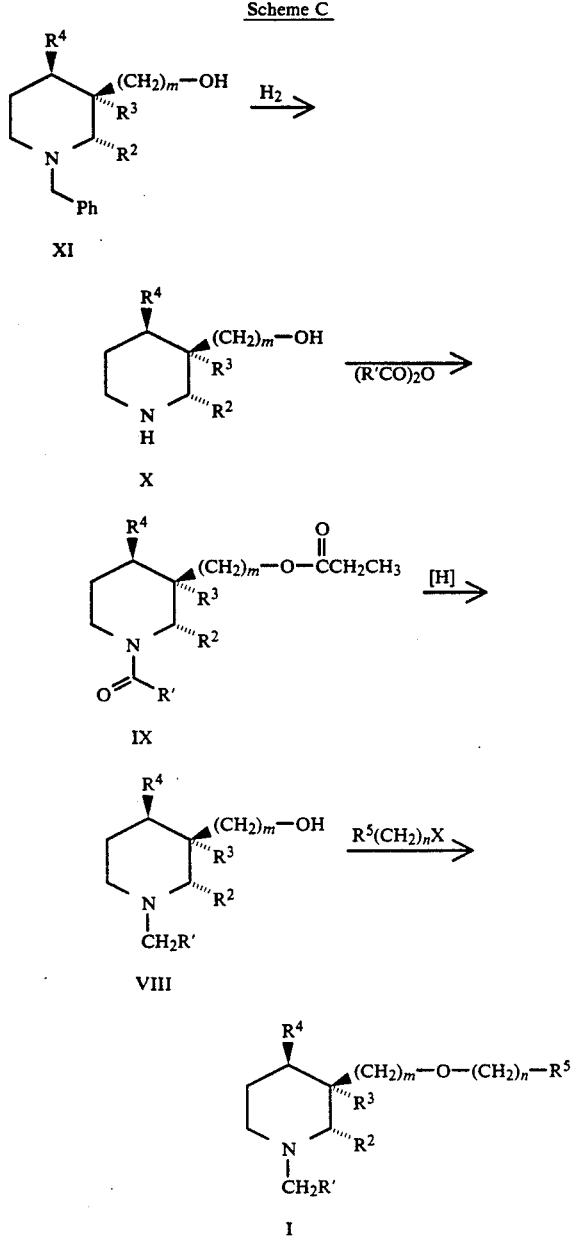

Scheme C

XI

X

IX

VIII

I

A suitably substituted 1-phenylmethyl-3-piperidineethanol or propanol (XI, m is two or three) in hydrogenated at a hydrogen pressure of about 50 psi, in an alcoholic solvent, e.g. ethanol, in the presence of a catalyst, preferably palladium on carbon, to produce the corresponding 3-piperidineethanol or propanol of Formula X. The compound of Formula X is treated with an excess of a suitable anhydride, (R'CO)₂O wherein R' is lower-alkyl, in the presence of an excess of a base, e.g. triethylamine, additionally in the presence of about 1 to about 2 mole percent of a catalyst, preferably dimethylaminopyridine, in a suitable solvent, such as dichloromethane, at about 25° C., to produce a 1-(1-oxo-lower-alkyl)-3-piperidineethyl or propyl propanoate of Formula IX. Treatment of this latter derivative with an excess of a reducing agent, e.g. lithium aluminum hydride, in a solvent such as tetrahydrofuran, at a temperature in the range of about 25° C. up to the boiling point of the solvent used, produces the 1-lower-alkyl-3-piperidineethanol or propanol derivative of Formula VIII which can be converted into the compounds of Formula I using the alkylation procedures described in Schemes A and B for the conversion of the compounds of Formula II and V to the compounds of Formula I.

In those instances wherein it is desirable to prepare a compound of the Formula I wherein $R^1$ is isopropyl it is advantageous to proceed as shown in Scheme D:

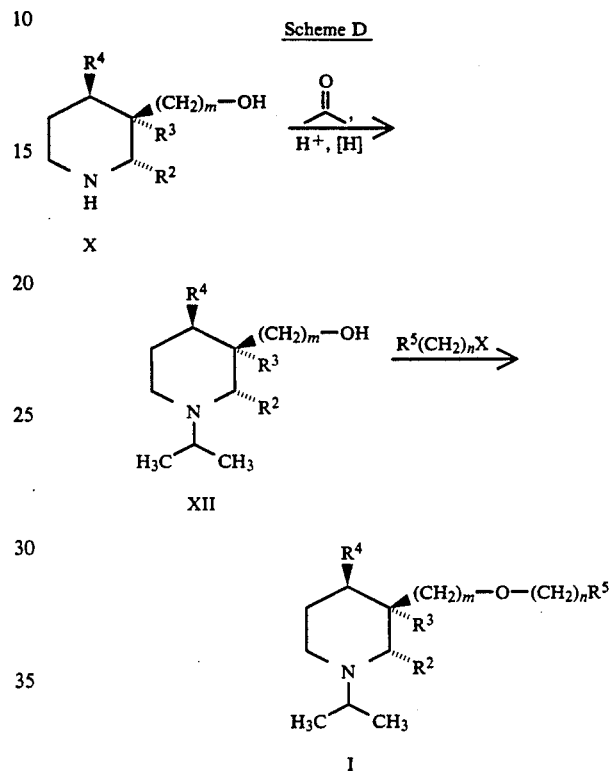

Scheme D

X

XII

I

A suitably substituted 3-piperidineethanol or propanol of Formula X is treated with an excess of acetone, in the presence of an excess of an acid, preferably acetic acid, additionally in the presence of a reducing agent, e.g. sodium cyanoborohydride, additionally in the presence of 3A° molecular sieves (about 30 g per 70 mmol of substrate), in an alcoholic solvent, preferably methanol, at about 25° C. to produce the 1-isopropyl-3-piperidineethanol or propanol of Formula XII, which can be converted into the compounds of Formula I using the alkylation procedures described in Schemes A and B for the conversion of compounds of Formula II and V to the compounds of Formula I.

The dilower-alkyl 2-azabicyclo[2.2.2]octane-6,6-dicarboxylates of Formula IV required for the synthesis of the compounds of Formula I wherein m is three are prepared as shown in Scheme E:

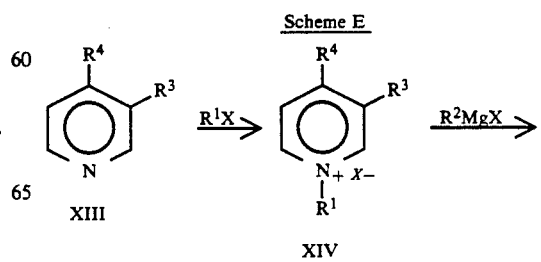

Scheme E

XIII

XIV

-continued
Scheme E

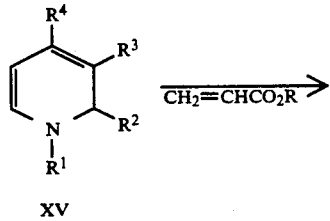

XV

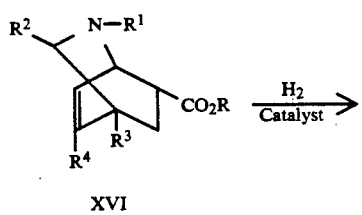

XVI

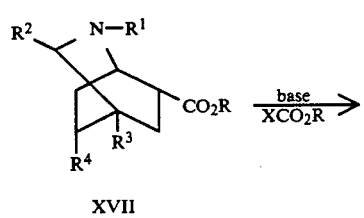

XVII

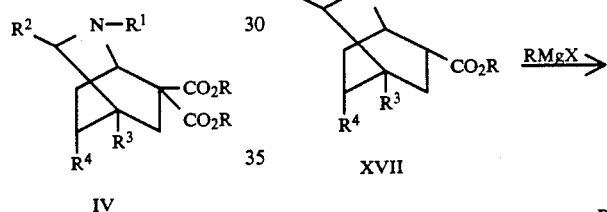

IV

A suitably substituted pyridine derivative (XIII) is treated with an appropriate alkylating agent, $R^1X$, in an alcoholic solvent, e.g. isopropanol, at a temperature in the range of from about 25° C. up to the boiling point of the solvent used to afford a pyridinium salt of the Formula XIV. The pyridinium salt is treated with an excess of an appropriate Grignard reagent, $R^2MgX$, in a solvent such as ether, at a temperature in the range of from about 0° C. up to about 25° C. to afford a 1,2-dihydropyridine of Formula XV. The 1,2-dihydropyridine (XV) is treated with a lower-alkyl acrylate, $CH_2=CHCO_2R$ wherein R is lower-alkyl, preferably ethyl, in a solvent such as toluene, at a temperature in the range of from about 25° C. up to the boiling point of the solvent used to afford a lower-alkyl 2-azabicyclo[2.2.2]oct-7-ene-6-carboxylate of Formula XVI. The compound of Formula XVI or acid-addition salt thereof, e.g. the hydrochloride, can be hydrogenated at a hydrogen pressure of from about 15 psi to about 50 psi, in the presence of a catalyst, preferably palladium on carbon, in an alcoholic solvent, e.g. methanol or ethanol to afford the lower-alkyl 2-azabicyclo[2.2.2]octane-6-carboxylates of Formula XVII. The compound of Formula XVII can then be treated with an an excess of a base, preferably lithium diisopropylamide, followed by treatment with an excess of an appropriate lower-alkyl haloformate, $XCO_2R$ wherein R is lower-alkyl, preferably ethyl chloroformate, in a solvent such as tetrahydrofuran, at a temperature in the range of from about −78° C. up to about 25° C. to afford the dilower-alkyl 2-azabicyclo[2.2.2]octane-6,6-dicarboxylates of Formula IV.

In those instances wherein a compound of the Formula XVI is used in which $R^1$ is benzyl, debenzylation also occurs under the hydrogenation reaction conditions described in Scheme E to produce a compound of the Formula XVII wherein $R^1$ is hydrogen. An appropriate $R^1$ substituent can be reintroduced into the compounds of Formula XVII by treating the compound of Formula XVII or acid-addition salt thereof, e.g. the hydrochloride, wherein $R^1$ is hydrogen (a) with an excess of formaldehyde and an excess of a base, preferably triethylamine, in an alcoholic solvent, e.g. ethanol, the presence of about 15 psi to about 50 psi of hydrogen pressure to afford a compound of Formula XVII wherein $R^1$ is methyl; or (b) with an excess of an appropriate alkylating agent, $R^1X$, in the presence of an excess of a base, such as potassium carbonate, in a solvent such as acetonitrile, at a temperature in the range of from about 25° C. up to the boiling point of the solvent used.

The 2-azabicyclo[2.2.2]octane-6-lower-alkanol of Formula VII required for the synthesis of the compounds of Formula I wherein m is two are prepared as shown in Scheme F:

Scheme F

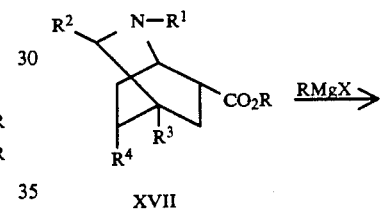

XVII

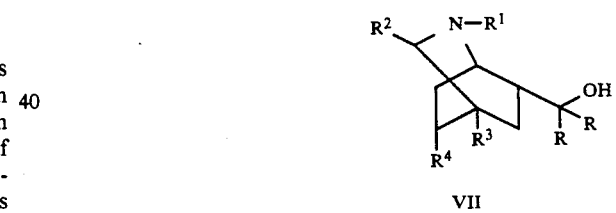

VII

A suitably substituted lower-alkyl 2-azabicyclo[2.2.2]octane-6-carboxylate of Formula XVII is treated with an excess of an appropriate Grignard reagent, RMgX wherein R is lower-alkyl, in a solvent, such as ether, at a temperature in the range of about 25° C. up to the boiling point of the solvent used, to afford the desired compound of Formula VII.

The appropriately substituted anhydride $(R'CO)_2O$, alkylating agent $(R^5(CH_2)_nX)$, pyridine (XIII), alkylating agent $(R^1X)$, Grignard reagent $(R^2MgX)$, lower-alkylacrylate $(CH_2=CHCO_2R)$, lower-alkyl haloformate $(XCO_2R)$, and Grignard reagent (RMgX), are either commercially available or can be prepared by procedures well known in the art.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, is precipitated with a second organic solvent or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by ion exchange procedures.

The structures of the compounds of the invention were established by the mode of synthesis, by elemental analysis, and by infrared, ultraviolet, nuclear magnetic resonance and mass spectroscopy. The course of the reactions and the identity and homogeneity of the products were assessed by thin layer chromatography (TLC) or gas-liquid chromatography (GLC).

The following examples will further illustrate the invention without, however, limiting it thereto. The abbreviation THF stands for tetrahydrofuran, HCl stands for hydrochloric acid, $CH_2Cl_2$ stands for dichloromethane, $NH_4Cl$ stands for ammonium chloride, $MgSO_4$ stands for magnesium sulfate, $Na_2SO_4$ stands for sodium sulfate, $NaHCO_3$ stands for sodium bicarbonate, $K_2CO_3$ stands for potassium carbonate, and NAOH stands for sodium hydroxide.

PREPARATION OF STARING MATERIAL

Preparation 1

(a)

A mixture of 3, 4-lutidine (112 mL, 1. 0 mole), benzyl chloride (115 mL, 1.0 mole) and isopropanol (500 mL) was refluxed under nitrogen for 5 hours and then was stirred at room temperature for 60 hours. The mixture was diluted with ether and the resulting white precipitate was filtered and dried to afford 178.3 g (76%) of N-(phenylmethyl)-3,4-dimethylipyridinium chloride.

(b)

A solution of methyl iodide (112 mL, 1.8 mole) in ether (225 mL) was added dropwise to a suspension of magnesium turnings (44 g, 1.8 mole) in ether (225 ml) under nitrogen over a period of 1 hour. The mixture was stirred at room temperature for 1 hour, transferred into a 1000 mL addition funnel and then was added to a suspension of N-(phenylmethyl)-3,4-dimethylpyridinium chloride (350.7 g, 1.5 mole) in ether (1500 mL) under a nitrogen atmosphere. The reaction mixture was stirred at room temperature for 24 hours and was then poured into a solution of saturated ammonium chloride (3 L). The organic layer was separated and the aqueous layer was extracted with ether (1000 mL). The combined ether layers were washed with water (500 mL), then brine (500 mL) and were dried over sodium sulfate and potassium carbonate-. The solvent was removed in vacuo to afford 284.1 g (76%) of 1,2-dihydro-N-(phenylmethyl)-2,3,4-trimethylpyridine, as an amber oil.

(c)

A solution of 1,2-dihydro-N-(phenylmethyl)-2,3,4-trimethylpyridine (284.1 g, 1.14 mole) in toluene (3000 mL) under nitrogen was treated with ethyl acrylate (162 mL, 1.5 mole). The mixture was refluxed for 21 hours and the solvent was removed in vacuo. The residue was dissolved in ethanol (300 mL), treated with 10 N ethanolic-HCl (20 mL) and diluted with ether. A precipitate formed, which was collected by filtration and recrystallized from ethanol (150 mL)/ether (1400 mL) to afford 117.5 g (22%) of ethyl 3,4,8-trimethyl-2-(phenylmethyl)-2-azabicyclo-2.2.2]-oct-7-ene-6-carboxylate hydrochloride as a white powder, m.p. 184–186° C. The mother liquor from the above recrystallization was treated with concentrated ammonium hydroxide (30 mL) and water (500 mL). The organic layer was separated, washed with brine and dried over potassium carbonate. The solvent was removed in vacuo and the residue was purified by column chromatography on silica eluting with ethyl acetate/hexane (25/75). The residue was dissolved in ethanol (50 mL), treated with 10.5 N ethanolic-HCl (10 mL) and diluted with ether (1200 mL). The product was collected by filtration and recrystallized from ethanol/ether to afford an additional 131.2 g of the product for a total yield of 47%.

(d)

A mixture of ethyl 3,4,8-trimethyl-2- (phenylmethyl) -2-azabicyclo[2.2.2]-oct-7-ene-6-carboxylate hydrochloride (17.4 g, 49.7 mol), 10% palladium on carbon (1.7 g) and ethanol (200 mL) was hydrogenated on a Parr hydrogenator at 50 psi for 6 hours. The mixture was removed from the Parr hydrogenator, cooled to 0° C. and triethylamine (7.0 mL, 50 mmol), followed by 37% formaldehyde (4.1 mL, 55 mmol) were added. The mixture was then placed back on the Parr hydrogenator at 50 psi for 1 hour. The reaction mixture was removed from the Parr hydrogenator, the catalyst was removed by filtration and the solvent was removed in vacuo. The residue was dissolved in water, basified with concentrated ammonium hydroxide (20 mL) and extracted with ether (3×300 mL). The combined organic layers were washed with brine (50 mL), dried over potassium carbonate and concentrated in vacuo to afford 11.5 g (96%) of ethyl 2,3,4,8-tetramethyl-2-azabicyclo[2.2.2]-octane-6-carboxylate as a pale yellow oil.

(e)

To a solution of diisopropylamine (3.0 mL, 22 mmol) in THF (34 mL) at 0° C. under nitrogen was added n-BuLi (8.8 mL, 22 mmol, 2.5 M in hexane). A solution of ethyl 2,3,4,8-tetramethyl-2-azabicyclo[2.2.2]octane-6-carboxylate (4.8 g, 20 mmol) in THF (46 mL) was added to the mixture and the reaction was stirred at 0° C. for 1 hour. Ethyl chloroformate (2.3 mL, 24 mmol) in THF (3 mL) was then added and the mixture was stirred for 15 minutes. The reaction mixture was diluted with saturated ammonium chloride and partitioned between water and ether. The aqueous layer was extracted with ether (2×) and the combined organic layers were dried over anhydrous MgSO$_4$. The solvent was removed in vacuo and the residue was purified by column chromatography on silica eluting with ether/hexane (15/85) to afford 3.9 g (63%) of diethyl 2,3,4,8-tetramethyl-2-azabicyclo[2.2.2]octane-6,6-dicarboxylate as a yellow oil.

Preparation 2

(a)

A mixture of ethyl 3,4,8-trimethyl-2-(phenylmethyl)-2-azabicyclo[2.2.2]-oct-7-ene-6-carboxylate hydrochloride (26.2 g, 75 mmol), 10% palladium on carbon (2.6 g) and ethanol (200 mL) were placed on a Parr hydrogenator at 50 psi for 3.5 hours. The catalyst was removed by filtration and the solvent was removed in vacuo to afford crude ethyl 3,4,8-trimethyl-2-azabicyclo[2.2.2]-octane-6-carboxylate hydrochloride as a yellow oil, which was used directly in the next step.

(b)

A mixture of the above crude product (approximately 75 mmol), potassium carbonate (104 g, 0.75 mol), benzyl chloride (8.6 mL, 76 mmol) and acetonitrile (500 mL) were refluxed under nitrogen for 24 hours. The reaction mixture was filtered and the solvent was removed in vacuo to afford 22.4 g (93%) of ethyl 3,4,8-trimethyl-2-(phenylmethyl)-2-azabicyclo[2.2.2]octane-6-carboxylate as a golden oil.

(c)

To a solution of diisopropylamine (13.2 mL, 94 mmol) in THF (175 mL) at −60° C. under nitrogen was added n-BuLi (36.2 mL, 94 mmol, 2.6 M hexane). The mixture was stirred for 30 minutes, cooled to −78° C. and ethyl 3,4,8-trimethyl-2-(phenylmethyl)-2-azabicyclo[2.2.2]octane-6-carboxylate (26.8 g, 85 mmol) in THF (225 mL) was added. The mixture was stirred for 3 hours, then ethyl chloroformate (8.96 mL, 94 mmol) in THF (20 mL) was added dropwise. The mixture was stirred for 24 hours, quenched with saturated NH$_4$Cl, and poured into water (1000 mL). The solution was extracted with ether (3×), and the organic layers were combined and dried over MgSO$_4$. The ether layer was treated with charcoal and the solvent was removed in vacuo to afford 32.1 g (97%) of diethyl 3,4,8-trimethyl-2-(phenylmethyl)-2-azabicyclo-[2.2.2]octane-6.6-dicarboxylate as a golden oil.

Preparation 3

Methyl iodide (138.4 g, 0.98 mole) was added dropwise over 1.5 hours to magnesium turnings (23.7 g, 0.98 mole) in ether (300 mL). The solution was diluted to a total volume of 1 liter and was stirred at room temperature for 2 hours. The solution was filtered through a glass wool plug into a second flask under nitrogen and a solution of ethyl 3,4,8-trimethyl-2-(phenylmethyl)-2-azabicyclo[2.2.2]-octane-6-carboxylate (87.9 g, 0.28 mole) in ether (400 mL) was added over 2 hours. The mixture was stirred at room temperature for 1 hour, poured into a mixture of saturated NH$_4$Cl (100 mL) and ice-water (100 mL) and the organic layer was separated. The aqueous phase was extracted with ether (2×700 mL) and the combined organic layers were washed with water (2×500 mL), then brine (500 mL) and were dried over anhydrous MgSO$_4$. The solvent was removed in vacuo to afford 82.5 g (98%) of α,α,3,4,8-pentamethyl-2-(phenylmethyl)-2-azabicyclo[2.2.2]octane-6-methanol.

Preparation 4

Following procedures similar to those described in preparations 1 a–e there was obtained:

(a)

358.4 g (82%) of N-benzyl-4-methylpyridinium chloride from 4-picoline (195 mL, 2 mol), benzyl chloride (230 mL, 2 mol) and isopropanol (1000 mL). The product was recrystallized from isopropanol (800 mL)/ether (1400 mL) to afford cream colored crystals.

(b)

1.2-Dihydro-N-benzyl-2,4-dimethylpyridinium, from N-benzyl-4-methylpyridinium chloride (330 g, 1.5 mmol), methyl iodide (112 mL, 1.8 mmol), magnesium turnings (44 g, 1.8 mmol), and ether (total of 2250 mL), which was used without purification directly in preparation 4c.

(c)

214.1 g (42%) of ethyl 3.8-dimethyl-2-(phenylmethyl)-2-azabicyclo[2.2.2]-oct-7-ene-6-carboxylate hydrochloride as cream colored crystals from 1,2-dihydro-N-benzyl-2,4-dimethylpyridine (298.7 g, 1.5 mol), ethyl acrylate (162 mL, 1.5 mol) and toluene (2 L). The product was recrystallized from ethanol/ acetonitrile/ether and had a melting point of 223–225° C.

(d)

43.5 g (96%) of ethyl 2,3,8-trimethyl-2-azabicyclo-[2.2.2]octane-6-carboxylate as a pale yellow oil from ethyl 3,8-dimethyl-2-(phenylmethyl)-2-azabicyclo[2.2.2]-oct-7-ene-6-carboxylate hydrochloride (67.2 g, 200 mmol), 10% palladium on carbon (3.6 g), ethanol (200 mL), methanol (200 mL), and water (40 mL) for step 1, and triethylamine (28 mL), and 37% aqueous formaldehyde (16.6 mL, 222.6 mmol) for step 2. The product was purified by a Kugelrohr distillation at 0.2 mm Hg and 65-80° C.

(e)

54.2 g (94%) of diethyl 2,3,8-trimethyl-2-azabicyclo-[2.2.2]octane-6,6-dicarboxylate as a pale yellow oil from ethyl 2,3,8-trimethyl-2-azabicyclo[2.2.2]octane-6-carboxylate (43.5 g, 193 mmol), diisopropylamine (30 mL, 213 mmol), n-BuLi (85 mL, 212.3 mmol, 2.5 u hexane), ethyl chloroformate (22.0 mL, 230 mmol) and THF (700 mL) The product was purified by column chromatography on silica eluting with hexane (100%) to hexane/ethyl acetate (4/1).

Preparation 5

(a)

Following a procedure similar to that described in Preparations 1a–c it is contemplated that ethyl 3,4-dimethyl-8-ethyl-2-(phenylmethyl)-2-azabicyclo[2.2.2]oct-7-ene-6-carboxylate and ethyl 3.8-diethyl-4-methyl-2-(phenylmethyl)-2-azabicyclo[2.2.2]oct-7-ene-6-carboxylate can be prepared from 4-ethyl-3-methyl pyridine and the appropriate Grignard reagent.

(b)

Following a procedure similar to that described in Preparation 2a-c it is contemplated that diethyl 3,4-dimethyl-8-ethyl-2-(phenylmethyl)-2-azabicyclo[2.2.2]octane-6-dicarboxylate and diethyl 3,8-diethyl-4-methyl-2-(phenylmethyl)-2-azabicyclo[2.2.2]octane-6-dicarboxylate can be prepared from the appropriate 2-azabicyclo[2.2.2]oct-7-ene-6-carboxylate of Preparation 5a.

PREPARATION OF FINAL PRODUCTS

Example 1

(a)

To diethyl 2,3,4,8-tetramethyl-2-azabicyclo[2.2.2]octane-6,6-dicarboxylate (121 g, 389 mmol) at 0° C. was added formic acid (121 mL, 3.2 mol), followed by triethylamine (179 mL, 1.3 mol). The mixture was slowly heated to 160° C. over a period of 2 hours and was stirred at 160° C. for 20 minutes. The mixture was cooled to room temperature, and allowed to stand under nitrogen for 24 hours. The mixture was basified by the addition of saturated $NaHCO_3$ and was extracted with ether (3×). The organic layers were combined, washed with saturated $NaHCO_3$ then brine and were dried over anhydrous $MgSO_4$. The solvent was removed in vacuo and the residue was taken up in 0.5 N HCl (500 mL) and washed with hexanes (3×). The aqueous layer was basified with concentrated $NH_4OH$ and extracted with ether (3×). The ether layer was dried over $MgSO_4$ and concentrated in vacuo to afford 34 g (36%) of ethyl 1,2,3,4-tetramethyl-3-piperidinepropanoate as a yellow oil. The combined aqueous phases were concentrated in vacuo and the residue was triturated with hot ethanol (800 mL at 70° C.). The solution was filtered, triturated with additional hot ethanol (300 mL) and filtered once again. The ethanol filtrates were combined, acidified with concentrated $H_2SO_4$ and refluxed for 24 hours under nitrogen. The solution was basified with concentrated $NH_4OH$ and extracted with ether (3×). The ether layers were combined, washed with saturated $NaHCO_3$ (2×) and dried over $MgSO_4$. The solvent was removed in vacuo to afford 28.5 g of additional product for a total yield of 62.5 g (67%). The product was treated with p-toluenesulfonic acid to afford ethyl 1,2,3,4-tetramethyl-3-piperidine-propanoate p-tolulenesulfonate as a white powder, m.p. 171-171.5° C.

(b)

A solution of ethyl 1,2,3,4-tetramethyl-3-piperidinepropanoate (25.0 g, 104 mmol) in THF (350 mL)) under a nitrogen atmosphere was cooled to 0° C. and lithium aluminum hydride (3.9 g, 100 mmol) was added in portions over 15 minutes. The reaction mixture was warmed slowly to room temperature and was stirred for 24 hours. The mixture was cooled to 0° C. and quenched with saturated $Na_2SO_4$ (20 mL) The mixture was stirred for 45 minutes, then anhydrous $Na_2SO_4$ (40 g) was added and the mixture was stirred for an additional 1.5 hours. The aluminum salts were removed by filtration and the filtrate was concentrated in vacuo. The residue was purified by Kugelrohr distillation at 0.7 mm Hg and 100-115° C. to afford 20.1 g (97%) of 3-(1,2,3,4-tetramethyl-3-piperidine)propanol.

(c)

Potassium hydride (3.8 g, 33 mmol) was washed with dry hexane (2×10 mL) and suspended in THF (60 mL) under a nitrogen atmosphere and 1,2,3,4-tetramethyl-3-piperidinepropanol (6.0 g, 30 mole) in THF (50 mL) was added dropwise over 10 minutes. The mixture was stirred at room temperature for 45 minutes then approximately 5 mole percent of tetrabutylammonium iodide, followed by cyclopropylmethyl bromide (4.5 g, 33 mmol) in THF (20 mL) was added. The mixture was stirred for 24 hours, diluted with ether and washed with brine (3×50 mL]. The organic layer was separated, dried over $Na_2SO_4$ and concentrated in vacuo. The residue was combined with additional crude 3-[3-(cyclopropylmethoxy)propyl)1,2,3,4-tetramethylpiperidine which was obtained from a similar experimental run but starting with 1.0 g of 1,2,3,4-tetramethyl-3-piperidinepropanol, and the mixture was purified by column chromatography on silica eluting with 10% ether/hexanes to 1% isopropylamine/10% ether/hexanes to afford 3.8 g(50%) of 3-[3-(cyclopropylmethoxy)propyl]1,2,3,4-tetramethylpiperidine. The product was dissolved in ethanol, treated with 7.2 U ethereal·HCl and diluted with ether to afford 3.2 g of the hydrochloride salt as a cream colored solid. The salt was recrystallized from ethanol/ether and had a melting point of 127-128° C.

Example 2

(a)

A mixture of diethyl 2,3,8-trimethyl-2-azabicyclo[2.2.2]octane-6-dicarboxylate (54.2 g, 182 mmol), formic acid (140 mL) and triethylamine (210 mL) were heated to 160° C. for 45 minutes. The reaction mixture was cooled, diluted with water (300 mL) and basified with ammonium hydroxide. The mixture was extracted with ether (3×300 mL), and the organic layer was dried over $Na_2SO_4$. Removal of the solvents in vacuo and analysis of the residue indicated that the reaction had not gone to completion. The residue was then resubjected to the above-mentioned reaction conditions for a time of four hours to afford 27.3 g (66%) of ethyl 3-(1,2,4-trimethyl-3-piperidine)propanoate which was used directly in the next step without further purification. The aqueous layers were combined, concentrated to dryness and triturated with ethanol (2×500 mL) The mixture was filtered, concentrated to approximately 250 mL, filtered again and concentrated in vacuo to afford a yellow oil. The oil was dissolved in ethanol (500 mL) and treated with concentrated $H_2SO_4$ until a Ph=1.5 was obtained. The mixture was once again filtered to remove any precipitated salts, the salts were washed with ethanol (2×250 mL) and the resulting solution was refluxed for 16 hours. The solvent was concentrated in vacuo, the residue was dissolved in water (500 mL) and the mixture was neutralized with ammonium chloride. The mixture was extracted with ether (3×300 mL), and the ether extracts were combined, washed with brine (100 mL), dried over anhydrous $MgSO_4$ and concentrated in vacuo to afford an additional 8.4 g of product. The crude product was combined with an additional 7.6 g of crude product from a similar experimental run, and the mixture (16 g) was purified by a Kugelrohr distillation at 80-95° C. and 0.4 mm Hg, followed by column chromatography on silica gel eluting with 0.5% isopropylamine/hexane to 2% isopropylamine/hexane to afford 12.2 g of purified product. The product was dissolved in ether, treated with 6.2 N ethereal·HCl and diluted with acetonitrile to afford 11.4 g of the hydrochloride salt, m.p. 88-90° C.

(b)

Following a procedure similar to that described in Example 1b, 21.6 g (97%) of 1,2,4-trimethyl-3-piperidinepropanol was obtained from ethyl 1,2,4-trimethyl-3-piperidinepropanoate (27.1 g, 120 mmol), lithium aluminum hydride (4.6 g, 120 mmol) and THF (500 mL). The product was purified by a Kugelrohr distillation at 0.1 mm Hg and 70-80° C.

(c)

Following a procedure similar to that described in Example 1c, 8.1 g (45%) of 3-[3-(cyclopropylmethoxy)-propyl]1,2,4-trimethylpiperidine was obtained as a golden oil from 1,2,4-trimethyl-3-piperidinepropanol (13.9 g, 75 mmol), potassium hydride (3.6 g, 90 mmol), THF (500 mL), tetrabutylammonium iodide (1.2 g), and cyclopropylmethyl bromide (10.6 g, 79 mmol). The product was purified by medium pressure liquid chromatography eluting with 2.5% isopropylamine/hexane. The product was dissolved in ethanol (5 mL), treated with 6.2 N ethereal·HCl and diluted with ether to afford an oil which was crystallized from acetonitrile/ether to afford 7.3 g of the hydrochloride salt as a tan solid. The salt was recrystallized from isopropyl acetate and had a melting point of 81-82° C.

Example 3

(a)

Following a procedure similar to that described in Example 2a, 10.0 g ( 9 8 % )of ethyl 2,3,4-trimethyl-1-(phenylmethyl)-3-piperidinepropanoate was obtained from diethyl 3,4,8-trimethyl-2-(phenylmethyl)-2-azabicyclo[2.2.2]octane-6-dicarboxylate of preparation 2C (12.5 g, 32.0 mmol), formic acid (11.0 mL) and triethylamine (14.7 mL). The product was treated with ethanolic HCl, and the resulting solid was recrystallized from ethanol/ether to afford 5.1 g of the hydrochloride salt as a white powder, m.p. 130.5-132.5° C.

(b)

Following a procedure similar to that described in Example 1b, 51.1 g (quantitative) of 2,3,4-trimethyl-1-(phenylmethyl)-3-piperidinepropanol was obtained from ethyl 2,3,4-trimethyl-1-(phenylmethyl)-3-piperidinepropanoate (57.3 g, 180 mmol), lithium aluminum hydride (7.6 g, 200 mmol) and THF (600 mL). The product was used directly in the next step without further purification.

(c)

A mixture of 2,3,4-trimethyl-1-(phenylmethyl)-3-piperidinepropanol (45.0 g, 163 mmol), ethanol (200 mL) and 10% palladium on carbon (4.5 g) was placed on a Parr hydrogenator at 50 psi of hydrogen pressure until hydrogen uptake ceased. The catalyst was removed by filtration and the filtrate was concentrated in vacuo. The residue was crystallized from ether to afford 24.9 g (82%) of 2.3.4-trimethyl-3-piperidinepropanol. The product was recrystallized from ethyl acetate and had a melting point of 89-91° C.

(d)

A mixture of 2,3,4-trimethyl-3-piperidinepropanol (10.2 g, 55 mmol), propionic anhydride (25 mL), triethylamine (50 mL), dichloromethane (200 mL) and dimethylaminopyridine (0.1 g) was stirred at room temperature for 24 hours. The solvent was removed in vacuo and the residue was dissolved in ether (600 mL), washed with NaHCO3 (3×200 mL), then brine (200 mL). The organic layer was dried over Na2SO4 and concentrated in vacuo to afford 20.1 g of crude product. 2.0 g of the crude product was purified by column chromatography on silica eluting with 10% ether/hexane to afford 1.5 g of 2,3,4-trimethyl-1-(1-oxopropyl)-3-piperidinepropyl propanoate as a colorless oil, and the remaining 18.1 g was used directly in the next step without further purification.

(e)

Following a procedure similar to that described in Example 1b, 7.2 g (52%) of 2. 3. 4-trimethyl-1-propyl-3-piperidinepropanol was obtained from 2,3,4-trimethyl-1-(1-oxopropyl)-3-piperidinepropyl propanoate (18.1 g, 61 mmol), lithium aluminum hydride (7.6 g, 200 mmol) and THF (500 mL). The product was purified by column chromatography on silica eluting with 2% isopropylamine/hexane.

(f)

Following a procedure similar to that described in Example 1c, 8.7 g (100%) of 3-[3-(cyclopropylmethoxy)propyl]-2,3,4-trimethyl-1-propylpiperidine was obtained as a yellow oil from 2,3,4-trimethyl-1-propyl-3-piperidinepropanol (7.1 g, 31 mmol), potassium hydride (4.3 g, 37 mmol), THF (150 mL), tetrabutylammonium iodide (0.240 g) and cyclopropylmethyl bromide (4 mL, 40 mmol) . The product was purified by a Kugelrohr distillation at 0.2 mm Hg and 100-105° C. The purified product was dissolved in ether, and treated with 4.8 N ethereal·HCl to afford 9.3 g of the hydrochloride salt as a white powder, m.p. 138-140° C.

Example 4

Following a procedure similar to that described in Example 1c, 6.0 g (84%) of 3-[3-(cycloprolmethoxy)-propyl]-2,3,4-trimethyl-1-(phenylmethyl)piperidine was obtained as a colorless oil from 2,3,4-trimethyl-1-(phenylmethyl)-3-piperidinepropanol (6.0 g, 21.8 mmol), potassium hydride (3.0 g, 26 mmol), THF (100 mL), tetrabutylammonium iodide (0.080 g) and cyclopropylmethyl bromide (2.3 mL, 24 mmol). The product was purified by column chromatography on silica eluting with 5% ethyl acetate/hexane to 10% ethyl acetate/hexane. The purified product was dissolved in ether and treated with 4.8 N ethereal·HCl to afford 6.2 g of the hydrochloride salt as a white powder, m.p. 132-133° C.

Example 5

(a)

A mixture of 2,3,4-trimethyl-3-piperidinepropanol (13.0 g, 70 mmol), acetone (400 mL), methanol (300 mL), sodium cyanoborohydride (4.4 g, 70 mmol), 3A molecular sieves (30 g) and acetic acid (4.0 mL, 70 mmol) was stirred under a nitrogen atmosphere for 2 hours. The pH was readjusted to a pH of 5 by the addition of 1.5 mL of additional acetic acid and the reaction mixture was stirred for 24 hours. The reaction mixture was filtered and the filtrate was concentrated in vacuo. The residue was dissolved in water (200 mL) and acetone (20 mL) and was acidified with concentrated hydrochloric acid. The mixture was basified with 10% NAOH and extracted with ether (4×300 mL). The ether extracts were combined, washed with brine and dried over $Na_2SO_4$. The solvent was removed in vacuo and the residue was purified by a Kugelrohr distillation at 0.1 mm Hg and 100–110° C. to afford 15.7 g (99%) of 2,3. 4-trimethyl-l- (1-methylethyl)-3-piperidinepropanol as a colorless oil.

(b)

Following a procedure similar to that described in Example 1c, 13.9 g (82%) of 3-[3-(cyclopropylmethoxy)propyl]-2,3,4-trimethyl-1-(1-methylethyl)piperidine was obtained from 2,3,4-trimethyl-l-(l-methylethyl)-3-piperidinepropanol (13.6 g, 60 mmol), potassium hydride (8.3 g, 72 mmol), THF (400 mL), tetrabutylammonium iodide (0.44 g) and cyclopropylmethyl bromide (6.4 mL, 66 mmol). The product was purified by column chromatography on silica eluting with 2% isopropylamine/hexane. The purified product was dissolved in ether and treated with 4.8 N ethereal·HCl to afford 13.6 g of the hydrochloride salt as a white solid. The salt was recrystallized from ethyl acetate/ether and had a melting point of 118.5–120° C.

Example 6

Potassium hydride (5.0 g, 0.125 mol) was washed with dry hexane and suspended in THF (80 mL) under a nitrogen atmosphere and 1,2,3,4-tetramethyl-3-piperidinepropanol (10.0 g, 0.05 mol) was added. The mixture was stirred at room temperature for 24 hours, then allyl bromide (12.1 g, 0.1 mol) was added at 0° C. The mixture was stirred for 24 hours and saturated NH4Cl (5 mL), and water were added. The solvent was removed in vacuo, 35% sodium hydroxide was added and the mixture was extracted with ether. The organic layer was dried over $K_2CO_3$ and the solvent was removed in vacuo to afford crude 1,2,3,4-tetramethyl-3-r3-(2-propenyloxy)propyl]piperidine as an oil. The crude product was dissolved in ether and treated with ethereal·HCl to afford 10.0 g of the hydrochloride salt as a tan powder, m.p. 130–132° C.

Example 7

Following a procedure similar to that described in Example 6, crude 1,2,3,4-tetramethyl-3-13-(2-propenyloxy)propyl]piperidine was obtained as a red oil from 1,2,3,4-tetramethyl-3-piperidinepropanol (19.9 g, 0.1 mol), potassium hydride (10.0 g, 0.25 mol), THF (200 mL) and propargyl chloride (37.2 g, 0.5 mol). The crude product was dissolved in ether and treated with ethereal·HCl to afford 7.9 g of the hydrochloride salt as a white solid, m.p. 143–145° C. when recrystallized from acetonitrile/isopropyl acetate.

Example 8

(a)

To formic acid (320 mL, 8.5 mole) at 0° C. was added dropwise triethylamine (480 mL, 3.4 mole) over 1.5 hours. $a,a$,3,4,8-Pentamethyl-2-(phenylmethyl)-2-azabicyclo[2.2.2]octane-6-methanol (82.4 g, 0.27 mole) was added to the reaction mixture and the solution was heated at 120° C. for 20 hours, followed by heating at reflux for 26 hours. The mixture was cooled, poured into a mixture of NAOH (350 g) and water (2.5 L) and was extracted with ether (3×800 mL). The organic layers were combined, washed with water (2×1000 mL), then brine (1000 mL) and were dried over anhydrous $MgSO_4$. The solvent was removed in vacuo, the residue was treated with ethereal·HCl and the product was collected by filtration. The product was purified by recrystallization from tert-butylmethyl ether/$CH_2Cl_2$ to afford 76.1 g of 2,3,4-trimethyl-3-(3-methyl-2-buten-1-yl)-1-(phenylmethyl)piperidine hydrochloride as a light yellow solid, m.p. 170–171° C. when dried at 25° C. for 16 hours in high vacuum.

(b)

2,3,4-trimethyl-3-(3-methyl-2-buten-1-yl)-1-(phenylmethyl)piperidine hydrochloride (24.7 g, 76.7 mmol) was dissolved in ethanol (500 mL) and cooled to −78° C. ozone was bubbled into the reaction mixture until the solution turned blue and the mixture was purged with oxygen, then nitrogen until the solution turned colorless. Sodium borohydride (14.5 g, 383 mmol) was added to the reaction mixture while maintaining the temperature at −78° C. and the solution was stirred at −78° C. for 1 hour. The mixture was slowly warmed to room temperature over a period of 2 hours, 6 H HCl was added to acidify the solution and the solvent was removed in vacuo. The white residue was taken up in water, washed with ether (3×100 mL), basified with aqueous NAOH and extracted with methylene chloride (3×200 mL) The organic layer was dried over $Na_2SO_4$ and the solvent was removed in vacuo. The residue was taken up in ether (500 mL), dried over anhydrous $MgSO_4$ and the solvent was removed in vacuo to afford 19.1 g (95%) of 2,3,4-trimethyl-1-(phenylmethyl)-3-piperidineethanol.

Example 9

To a suspension of 97% sodium hydride (2.6 g, 110 mmol) in THF (250 mL) under nitrogen was added dropwise a solution of 2,3,4-trimethyl-l-(phenylmethyl)-3-piperidineethanol (19.1 g, 73.1 mmol) in THF (50 mL) over 10 minutes. The mixture was stirred at room temperature for 1 hour and allyl bromide (10.6 g, 87.7 mmol), followed by tris[2-(2-methoxy)ethoxyethyllamine (1.2 g, 3.65 mmol) were added. The reaction mixture was heated to reflux for 18 hours and additional sodium hydride (3.0 9) and allyl bromide (2.0 mL) were added. The mixture was refluxed for an additional 5 hours, cooled to room temperature and added to water (250 mL). The mixture was extracted with ether (3×200 mL), the organic layer was washed with water (2×200 mL), then brine (200 mL) and the solvent was dried over anhydrous $MgSO_4$. The solvent was removed in vacuo and the residue was purified by column chromatography on silica eluting with hexane/isopropylamine (98/2) to afford 8.9 g (40%) of 2.3.4-trimethyl-1-(phenylmethyl)-3-12-(2-propenyloxy)ethyl]piperidine as a colorless oil.

Example 10

Following a procedure similar to that described in Example 2a–c it is contemplated that 3-[3-(cyclopropylmethoxy)propyl]-2,4-diethyl-3-methyl-1-(phenylmethyl)piperidine can be prepared from diethyl 3,8-diethyl-4-methyl-2-(phenylmethyl)-2-azabicyclo[2.2.2]octane-6,6-dicarboxylate.

Example 11

Following a procedure similar to that described in Example 2a-c it is contemplated that 3-[3-(cyclopropylmethoxy)propyl]-2,3-dimethyl-4-ethyl-1-(phenylmethyl)piperidine can be prepared from diethyl 3,4-dimethyl-8-ethyl-2-(phenylmethyl)-2-azabicyclo-[2.2.2]octane-6,6-dicarboxylate.

Example 12

Following a procedure similar to that described in Example 1c it is contemplated that 3-[3-(cyclohexylethoxy)propyl]-2,3,4-trimethyl-1-(phenylmethyl)piperidine and 3-[3-(cyclohexylpropoxy)propyl]-2,3,4-trimethyl-1-(phenylmethyl)piperidine can be prepared from 2,3,4-trimethyl-1-(phenylmethyl)-3-piperidinepropanol and the appropriate cyclohexylalkyl halide.

Example 13

Following a procedure similar to that described in Example 6, there was obtained 3-(3-methoxypropyl)-1,2,3,4-tetramethylpiperidine, from 1,2,3,4-tetramethyl-3-piperidinepropanol (5.0 g, 0.025 mol), potassium hydride (2.5 g, 0.062 mol), THF (80 mL) and dimethyl sulfate (6.3 g, 0.05 mol). The product was dissolved in ether and treated with ethereal·HCL to afford an orange oil. The orange oil was dissolved in isopropyl acetate and triturated with ether to afford the product as the hydrochloride salt, m.p. 166–168° C. when recrystallized from isopropylacetate/acetonitrile.

BIOLOGICAL TEST RESULTS

In standard biological test procedures, representative examples of the compounds of the invention have been found to bind with high affinity to sigma receptors, and are thus useful in the treatment of central nervous system disorders such as psychoses, dystonias, dyskinesias, Parkinson's syndrome, Huntington's chorea, Tourette syndrome and the like, especially psychoses, e.g. schizophrenic psychoses, manic depressive psychoses and the like.

The sigma receptor binding activity of representative compounds of the invention was demonstrated by following a procedure essentially as described by Hudkins and DeHaven-Hudkins, Life Sci. 1991, 49(17), 1229–1235.

Brain tissue was prepared from male Hartley guinea pigs (Hazelton Labs, Denver, Pa.) which were anesthetized with $CO_2$ and sacrificed by decapitation. All animal care and use procedures were in accord with the "Guide for the Care and Use of Laboratory Animals" (NIH Publ. No. 86-23, 1985). Homogenization was performed in 10 volumes (wt/vol) of 0.32 M sucrose with a Brinkmann Polytron at setting 5, 30 sec. The homogenate was centrifuged at 900×g for 10 min at 4° C., and the supernatant was collected and centrifuged at 22,000×g for 20 min at 4° C. The pellet was resuspended in 10 volumes of Tris-HCl buffer (50 mm, pH 7.4), incubated at 37° C. for 30 min, and centrifuged at 22,000×g for 20 min at 4° C. Following this, the pellet was resuspended in Tris buffer and frozen in 5–10 mL aliquots corresponding to a tissue concentration of 100 mg/ml, at −70° C. Binding characteristics of the membranes were stable for at least one month when stored at −70° C.

On the day of the assay, membrane aliquots were thawed, resuspended in fresh Tris-HCl buffer and stored on ice until use. Each assay tube contained 100 μL of [$^3$H]-(+)-pentazocine at a final concentration of approximately 0.5 nM or 100 μL of [$^3$H]di(2-tolyl)-guanidine (DTG) at a final concentration of approximately 4 nM, 100 μL of various concentrations of the compounds of interest, 500 μL of the tissue suspension and 300 μL of buffer to a final assay volume of 1 mL and a final tissue concentration of approximately 8 mg/tube, corresponding to approximately 0.15 mg protein/tube. Non-specific binding was defined by addition of a final concentration of 1 μM haloperidol to blank tubes for [$^3$H](+)-pentazocine assay or by addition of a final concentration of 10 μM haloperidol to blank tubes for [$^3$H]DTG assay. All tubes were incubated at 37° C. for 150 min in the [$^3$H](+) -pentazocine assay or at 25° C. for 90 min in the [$^3$H]DTG assay before termination of the reaction by rapid filtration over Whatman GF/B glass fiber filters that were presoaked in a solution of 0.5% polyethyleneimine for at least 1 hr prior to use. Filters were washed with three 4 ml volumes of cold Tris-HCl buffer.

Following addition of scintillation cocktail, samples were allowed to equilibrate for at least 4 hr. The amount of bound radioactivity was determined by liquid scintillation spectrometry using a Beckman LS 5000 TA liquid scintillation counter with an efficiency for tritium of approximately 60%. The results are reported as a percent (%) inhibition of binding at 10 μM.

Scatchard parameters and inhibition constants ($K_i$ values) for the binding of test compounds were also calculated using the EBDA/LIGAND program (McPherson, J. Pharmacol. Meth. 1985, 14, 213–228), purchased from Elsevier/Biosoft, Inc. The $K_i$ values are expressed as the mean or the mean ±SEM of at least two separate determinations performed in triplicate.

The following Table summarizes the results obtained from the testing of representative compounds of the invention.

TABLE 1

| | [$^3$H] (+)-Pentazocine | | [3H]DTG | |
|---|---|---|---|---|
| Example No. | Percent Inhibition | $K_i$ (nM) | Percent Inhibition | $K_i$ (nM) |
| 1b | 42 | — | 39 | — |
| 1c | 94 | 197 ± 32 | — | — |
| 2c | — | 5.0 ± 0.2 | — | — |
| 3c | — | 16723 | 23 | — |
| 3f | 99 | 45 ± 2 | — | — |
| 4 | — | 3.7 ± 0.4 | — | — |
| 5a | 17 | — | 30 | — |
| 5b | 91 | 435 ± 17 | — | — |
| 6 | 89 | 559 ± 64 | — | — |
| 7 | 76 | — | — | — |
| 9 | 99 | 300 ± 65 | — | — |
| 8b | 85 | — | — | — |
| 13 | — | 7669 | — | 11370 |

The compound of Example 4 was tested in vivo in the apomorphine-induced climbing assay and the apomorphine-induced stereotypy assay using the following procedures:

Male, Swiss-Webster mice (Taconic Farms, Germantown, N.Y.) weight 20–30 grams were grouped housed in colony facilities for a minimum of two days prior to testing. The colony facility was maintained on a 12 hour light/dark cycle (light: 0600–1800 hours) with water and Agway Prolab 100 rat chow available ad libitum. Each mouse was given an injection of test compound i.p. followed immediately by a s.c. injection of apomorphine 5.5 mg/kg or vehicle. All drugs were administered in a volume of 10 ml/kg body weight. The mice were then placed in individual cylindrical stainless steel climbing cages; 14.5 cm tall, 12 cm in diameter, with walls consisting of 1/16" O.D. bars spaced 0.8–1.0 cm apart, and were allowed to habituate to this environment for 20 minutes. Rating of climbing and stereotypy occurred every 30 seconds for ten minutes (e.g. 20–30 minutes post drug treatment) by an observer blind to treatment. The scale used for climbing was simply the number of paws contacting the bars (0–4). The stereotypy scale used (0–3) was that described previously (Peuch et al. European Journal Pharmacology 1978, 50, 291). Briefly, a (0) was scored for absence of any stereotypic behavior, infrequent stereotypic movements were scored as (1), a (2) was scored for permanent sniffing and a score of (3) indicated intense and continuous stereotypic behavior. Treatment means for the 10 minute totals were calculated for climbing and stereotypy. A Student's tetest was used to confirm a significant ($P<0.05$) increase in both behaviors following apomorphine treatment. Significant ($P<0.05$) antagonism as potentiation of the apomorphine-induced effect was identified using Dunnett's Test comparing each treatment group to apomorphine control using the computer program of Tallarida and Murray (Manual of Pharmacologic Calculation with Computer Programs, p. 145, Springer-Verlag, New York, 1987). A minimal effective dose (MED) for inhibition was determined for each parameter based on these analyses.

The compound of Example 4 had a MED for inhibition of 167 μmol/kg in the apomorphine-induced climbing assay and did not affect stereotypic behavior in the apomorphine-induced stereotypy assay.

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

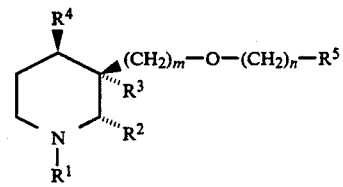

wherein:
$R^1$ is hydrogen, lower-alkyl or phenyl-lower-alkyl;
$R^2$ and $R^4$ are the same or different lower-alkyl;
$R^3$ is hydrogen or lower-alkyl;
m is two or three;
n is an integer from zero to three; and
$R^5$ is hydrogen, lower-alkyl, $C_3$–$C_7$-monocyclic-cycloalkyl, allyl, or propargyl;

or a pharmaceutically acceptable acid-addition salt thereof.

2. A compound according to claim 1 wherein $R^2$ and $R^4$ are the same lower-alkyl.

3. A compound according to claim 2 wherein $R^2$ and $R^4$ are methyl, and $R^3$ is hydrogen or methyl.

4. A compound according to claim 3 wherein $R^1$ is hydrogen, methyl, propyl, isopropyl, or benzyl; and n is zero or one.

5. A compound according to claim 4 wherein $R^5$ is hydrogen, methyl, cyclopropyl, allyl or propargyl.

6. 3-[3-(cyclopropylmethoxy)propyl]-2,3,4-trimethyl-1-(phenylmethyl)piperidine, or an acid-addition salt thereof according to claim 5.

7. 3-[3-(cyclopropylmethoxy)propyl]-1,2,4-trimethylpiperidine, or an acid-addition salt thereof according to claim 5.

8. A pharmaceutical composition which comprises an antipsychotically effective amount of a compound of the formula:

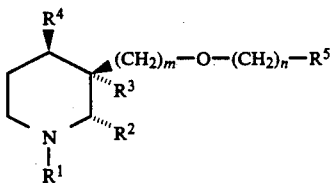

wherein:

$R^1$ is hydrogen, lower-alkyl or phenyl-lower-alkyl;

$R^2$ and $R^4$ are the same or different lower-alkyl;

$R^3$ is hydrogen or lower-alkyl;

m is two or three;

n is an integer from zero to three; and $R^5$ is hydrogen, lower-alkyl, $C_3$–$C_7$-monocyclic cycloalkyl, allyl, or propargyl;

or a pharmaceutically acceptable acid-addition salt thereof, together with a pharmaceutically acceptable carrier, adjuvant, diluent or vehicle.

9. A pharmaceutical composition according to claim 8 wherein $R^1$ is hydrogen, methyl, propyl, isopropyl or benzyl; $R^2$ and $R^4$ are methyl; $R^3$ is hydrogen or methyl; and n is zero or one.

10. A pharmaceutical composition according to claim 9 wherein the compound is 3-[3-(cyclopropylmethoxy)-propyl]-2,3,4-trimethyl-1-(phenylmethyl)piperidine, or an acid-addition salt thereof.

11. A pharmaceutical composition according to claim 9 wherein the compound is 3-[3-(cyclopropylmethoxy)-propyl]-1,2,4-trimethylpiperidine, or an acid-addition salt thereof.

12. A method for the treatment of psychosis which comprises administering to a patient in need of such treatment an effective amount of a compound of the formula:

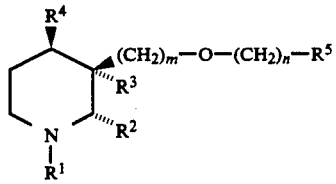

wherein:

13. A method according to claim 12 wherein $R^1$ is hydrogen, methyl, propyl, isopropyl, or benzyl; $R^2$ and $R^4$ are methyl; $R^3$ is hydrogen or methyl; and n is zero or one.

14. A method according to claim 13 wherein the compound is 3-[3-(cyclopropylmethoxy)propyl]-2,3,4-trimethyl-1-(phenylmethyl)piperidine, or an acid-addition salt thereof.

15. A method according to claim 13 wherein the compound is 3-[3-(cyclopropylmethoxy)propyl]-1,2,4-trimethylpiperidine, or an acid-addition salt thereof.

* * * * *

UNITED STATES PATENT AND TRADEMARK OFFICE
CERTIFICATE OF CORRECTION

PATENT NO.  : 5,290,789
DATED       : March 1, 1994
INVENTOR(S) : Diane L. DeHaven-Hudkins, et al.

It is certified that error appears in the above-identified patent and that said Letters Patent is hereby corrected as shown below:

Column 23, line 18: "tetest was" should read as -- t-test was --.

Column 26, line 18, claim 12 the portion of the text after the term "wherein:" has been omitted and should read as follows:

--$R^1$ is hydrogen, lower-alkyl or phenyl-lower-alkyl;
$R^2$ and $R^4$ are the same or different lower-alkyl;
$R^3$ is hydrogen or lower-alkyl;
m is two or three;
n is an integer from zero to three; and
$R^5$ is hydrogen, lower-alkyl, C3-C7-monocyclic cycloalkyl, allyl, or propargyl;
or a pharmaceutically acceptable acid-addition salt thereof. --

Signed and Sealed this

Thirtieth Day of August, 1994

*Attest:*

BRUCE LEHMAN

*Attesting Officer*   *Commissioner of Patents and Trademarks*